(12) United States Patent
Egts et al.

(10) Patent No.: US 11,724,057 B2
(45) Date of Patent: Aug. 15, 2023

(54) PROTECTIVE, SANITARY, SECURABLE NASAL CANNULA COVER

(71) Applicants: Melissa H. Egts, Stow, OH (US); David D. Egts, Stow, OH (US)

(72) Inventors: Melissa H. Egts, Stow, OH (US); David D. Egts, Stow, OH (US)

( * ) Notice: Subject to any disclaimer, the term of this patent is extended or adjusted under 35 U.S.C. 154(b) by 201 days.

(21) Appl. No.: 16/715,698

(22) Filed: Dec. 16, 2019

(65) Prior Publication Data
US 2021/0178101 A1   Jun. 17, 2021

(51) Int. Cl.
*A61M 16/06* (2006.01)
*A61B 50/00* (2016.01)

(52) U.S. Cl.
CPC ......... *A61M 16/0672* (2014.02); *A61B 50/00* (2016.02); *A61B 2050/0083* (2016.02); *A61M 2209/06* (2013.01)

(58) Field of Classification Search
CPC ........... A61M 16/0666–0677; A61M 2209/06; A61B 50/00; A61B 2050/0083
See application file for complete search history.

(56) References Cited

U.S. PATENT DOCUMENTS

| | | |
|---|---|---|
| 3,187,396 A | 6/1965 | Carroll |
| D247,345 S | 2/1978 | Mulholland |
| D309,960 S | 8/1990 | Applebaugh |
| D534,065 S | 12/2006 | Andre et al. |
| D577,990 S | 10/2008 | Andre et al. |
| D612,148 S | 3/2010 | Treece et al. |
| 7,798,332 B1 | 9/2010 | Brunet |
| 7,798,333 B2 | 9/2010 | Brunet |
| 8,746,251 B2 | 6/2014 | Besch et al. |
| 8,887,919 B2 | 11/2014 | Turner |
| D752,955 S | 4/2016 | Rowan |
| D775,937 S | 1/2017 | Davis |
| D781,416 S | 3/2017 | Racz et al. |
| 9,731,038 B2 | 8/2017 | Turner |
| D819,483 S | 6/2018 | Ciptak et al. |
| D832,692 S | 11/2018 | Wu et al. |

(Continued)

OTHER PUBLICATIONS

MyBoard Advisors acquires Hartfiel Medical as new client, posted at news-herald.com, earliest date available Sep. 18, 2021, [online], acquired on Mar. 15, 2022, Available on internet. url:https://www.news-herald.com/2021/09/18/myboard-advisors-acquires-hartfiel-medical-as-new-client/ (Year: 2021).

*Primary Examiner* — Rachel T Sippel
(74) *Attorney, Agent, or Firm* — Thompson Hine LLP

(57) ABSTRACT

A nasal cannula cover which includes a body having a cavity adapted to receive at least the prongs of a nasal cannula to protect the same from contaminants when the nasal cannula is not in use. Vents are present in the body to facilitate moisture removal from the cavity and discourage bacterial growth. The cover contains a nasal cannula connector with a fastener that temporarily connects the nasal cannula to the cover. The cover further includes an attachment fixture that facilitates connection of the cover to a surface, such as, but not limited to a strap of a bag that a portable oxygen concentrator is carried in, a cart that carries an oxygen tank or concentrator or even a surface in the home, for example a chain, doorknob or home oxygen source, so that the nasal cannula does not come in contact with any unsanitary surface.

22 Claims, 8 Drawing Sheets

(56) References Cited

U.S. PATENT DOCUMENTS

| | | |
|---|---|---|
| D833,264 S | 11/2018 | Wu et al. |
| D886,993 S | 6/2020 | Dwyer et al. |
| D890,924 S | 7/2020 | Godinez et al. |
| D896,371 S | 9/2020 | Azapagic et al. |
| D908,871 S | 1/2021 | Hu et al. |
| D909,187 S | 2/2021 | Hanke et al. |
| D917,422 S | 4/2021 | Chen |
| D921,887 S | 6/2021 | Hu et al. |
| D928,311 S | 8/2021 | McVaney |
| D935,864 S | 11/2021 | Janna |
| D938,953 S | 12/2021 | Nedelea et al. |
| D939,937 S | 1/2022 | Chou |
| D942,620 S | 2/2022 | Doerr |
| D943,094 S | 2/2022 | Doerr |
| 2004/0230108 A1* | 11/2004 | Melker ............... A61B 5/0261 600/340 |
| 2009/0101142 A1 | 4/2009 | Lang |
| 2009/0199858 A1 | 8/2009 | Hagberg et al. |
| 2011/0027231 A1 | 2/2011 | Francois |
| 2012/0160248 A1 | 6/2012 | McKinnon et al. |
| 2013/0306078 A1* | 11/2013 | Lanciotto .......... A61M 16/0666 128/207.18 |
| 2015/0034090 A1 | 2/2015 | Berger et al. |
| 2016/0015296 A1 | 1/2016 | Garaycochea |
| 2016/0339199 A1* | 11/2016 | Schaffer ............... A61M 16/14 |
| 2019/0209798 A1 | 7/2019 | Landrum |
| 2020/0330707 A1* | 10/2020 | Ellington, IV .... A61M 16/0003 |

* cited by examiner

PROTECTIVE, SANITARY, SECURABLE NASAL CANNULA COVER

FIELD OF THE INVENTION

The present invention relates to a nasal cannula cover. The cover includes a body having a cavity adapted to receive at least the prongs of a nasal cannula to protect the same from contaminants when the nasal cannula is not in use. Vents are present in the body to facilitate moisture removal from the cavity and discourage bacterial growth. The cover contains a nasal cannula connector with a fastener that temporarily connects the nasal cannula to the cover. The cover further includes an attachment fixture that facilitates connection of the cover to a surface, such as, but not limited to, a strap of a bag that a portable oxygen concentrator is carried in, a cart that carries an oxygen tank or concentrator or even a surface in the home, for example a chain, doorknob or home oxygen source, so that the nasal cannula does not come in contact with any unsanitary surface.

BACKGROUND OF THE INVENTION

Supplemental oxygen is delivered to patients with the use of a nasal cannula. A nasal cannula is a device consisting of hollow, flexible plastic tubing. One end connects to an oxygen supply line of the device that holds or generates the level of oxygen the patient needs. The other end delivers oxygen to the patient's nostrils via two prongs that are inserted into the patient's nose, one prong of the cannula resting inside each nostril.

Systems to delivery oxygen to a user include both home systems as well as portable systems. Portable systems such as portable oxygen concentrators and oxygen canisters are used to supply oxygen to the user outside the home and provide mobility. Each system uses a cannula. Oxygen concentrators utilize filters to remove contaminants from the air such as dust, hair, and bacteria and deliver a supply of clean oxygen to the user.

Similarly, a cannula cover prevents contact with unclean surfaces that may pollute the cannula nasal prongs when the user isn't wearing it. It also prevents contact with mold, fungus, and viruses on surfaces such as counters and floors upon which a cannula might come into contact. The cannula cover can be used with the dedicated cannula that is attached to the home source of oxygen or to the dedicated cannula attached to a mobile device, such as a portable oxygen concentrator or oxygen tank.

One of the inventors is a user of supplemental oxygen and has discovered, first-hand, problems associated with utilizing nasal cannula. For example, many users do not like to wear nasal cannula when eating. However, when not in use, the nasal cannula can fall onto the floor of a home or restaurant which can cause contact with dirt, mold, fungus, or other pathogens that can later be inhaled and may be dangerous to already compromised lungs.

Use of a nasal cannula with a portable oxygen generator while the user is mobile can cause additional problems. The bag or carrying case for the portable oxygen concentrator does not have a way to secure the nasal cannula for storage. One does not want to place the nasal cannula on the portable oxygen concentrator case or contact the case because the same may also be contaminated. Hanging the nasal cannula from the carrying case or placing it in the pocket of the carrying case are equally undesirable options because other objects such as a wallet, inhaler, tissues, etc. may already be present therein and contaminated.

Public restrooms also present another situation in which is it difficult to store the nasal cannula property. For women, the portable oxygen concentrator can be held on the lap, which is not comfortable. Men may need to have the use of their hands available to them or not want to hang the portable concentrator over their shoulder when using the bathroom to keep out of contact with bathroom fluids. One option is to hang it on a hook on the back of a restroom stall door. However, the length of the nasal cannula tubing may not always reach the toilet when hung on the door hook. This makes it necessary to temporarily remove the nasal cannula and hang it unsecurely on the bathroom stall hook or equally unsecured in a pocket of the case of the portable oxygen concentrator.

Even at home, a user may commonly hang the nasal cannula on anything conveniently nearby such as a doorknob, a water bottle sitting on a kitchen counter or even the back of a chair. In these situations, nasal cannula frequently come into contact with unclean surfaces or fall onto a floor which allows the nasal cannula to potentially come into contact with contaminants.

Therefore, problems to be solved relate to the necessity of protecting the nasal prongs of the nasal cannula from contaminants, at home, outside the home and even in a hospital setting.

Various devices to be utilized in association with nasal cannulas have been proposed in the art. For example, see U.S. Pat. Nos. 9,731,038, 8,887,919, 8,746,251, 7,798,332, D612,148, 2019/0209798, 2015/0034090 and 2009/0199858.

However, the prior art does not solve all of the problems noted above and a nasal cannula cover is still needed that is safe, convenient and is an inexpensive product that can protect a nasal cannula and prevent contaminants from entering the oxygen user's lungs and is an advancement over previous designs.

SUMMARY OF THE INVENTION

The problems noted above and others are solved by the nasal cannula cover of the present invention which provides sanitary storage for a nasal cannula when not in use. The cover is preferably of single piece construction and ergonomically designed, generally in the form of a semi-circle or partial oval. The cover includes a body having a cavity into which nasal prongs of a nasal cannula can be inserted. The cover also includes a nasal cannula connector, preferably two arms, that temporarily connect the nasal cannula to the cover. The nasal cannula can be inserted into the cover with little pressure and removed as easily with a slight pull or tug. Due to the presence of a cannula seat on the cover that conforms to the shape of the nasal cannula, the act of inserting the nasal cannula into the cover seals the cannula prongs within the body of the cover.

In yet a further embodiment of the invention, a divider is present in the cavity of the cover that separates the two prongs of the nasal cannula to prevent cross contamination.

In still another embodiment, an anti-microbial coating is provided on at least one portion of the nasal cannula cover, such as in the cavity thereof.

In still a further embodiment, the cover includes an attachment fixture including a handle that is formed on or connected to the body that facilitates connection of an object for hanging the cover during storage. Preferably the handle includes an aperture that extends completely through the body which is convenient for allowing a user to attach the cover utilizing a hook, Velcro® or other device that can facilitate attachment of the cover to another object, such as a strap or other part of case or bag for a portable oxygen concentrator. While the nasal cannula cover attaches to the strap of an oxygen carrying case or cart for easy access, it can also be attached to items in the home to include but not limited to a kitchen chair where a user commonly takes the cannula off to eat, bathroom doorknob where a user takes off the cannula to bathe and dress, and a home oxygen source for safe storage when the user switches to a mobile oxygen unit.

There are many inventive advancements in the design of the cover over previously published and patented designs. For example, the cover can be attached to an oxygen carrying case, bag or oxygen cart for easy access and portability. Further, the nasal cannula cover utilizes the cannulas own natural compressive properties to hold the prongs within the cavity of the cover and the nasal cannula itself securely in place on the cover, sealing the nasal cannula prongs in the cavity. In addition, the cover is preferably made from a single piece of material, preferably a polymer and is free of a lid and free of a hinge that can be broken. Also, the cover is easier to use than the prior art and the nasal cannula can be connected to the cover by simply pushing the cannula against the cover to seat the cannula in the nasal cannula connector and there is no need to open any lid or container. The cover is thus very easy to use, can be rapidly deployed, and is very convenient, particularly if the user has arthritis in one or more fingers.

Accordingly, in one aspect a nasal cannula cover for use with a nasal cannula is disclosed, comprising a body having a cavity extending a depth from an outer surface of the body into an interior portion of the body; a divider that separates the cavity into a first section adapted to accept a first prong of the nasal cannula and a second section adapted to accept a second prong of the nasal cannula; and a nasal cannula connector including a fastener that is adapted to releasably engage and connect the nasal cannula to the cover for storage of nasal prongs of the nasal cannula within the cavity.

In another aspect a nasal cannula cover for use with a nasal cannula is disclosed, comprising a body having a cavity extending a depth from an outer surface of the body into an interior portion of the body; a nasal cannula connector including a fastener that is adapted to releasably engage and connect the nasal cannula to the cover for storage; wherein the fastener includes a first arm located on a first side of the body adjacent the cavity and a second arm located on a second side of the body adjacent the cavity, wherein the first arm and second arm are adapted to releasably connect the nasal cannula therebetween.

For the avoidance of doubt, it is to be understood that while various embodiments of the invention are described individually, it should be clear two or more of the embodiments can and are often present in a single nasal cannula cover according to the invention.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
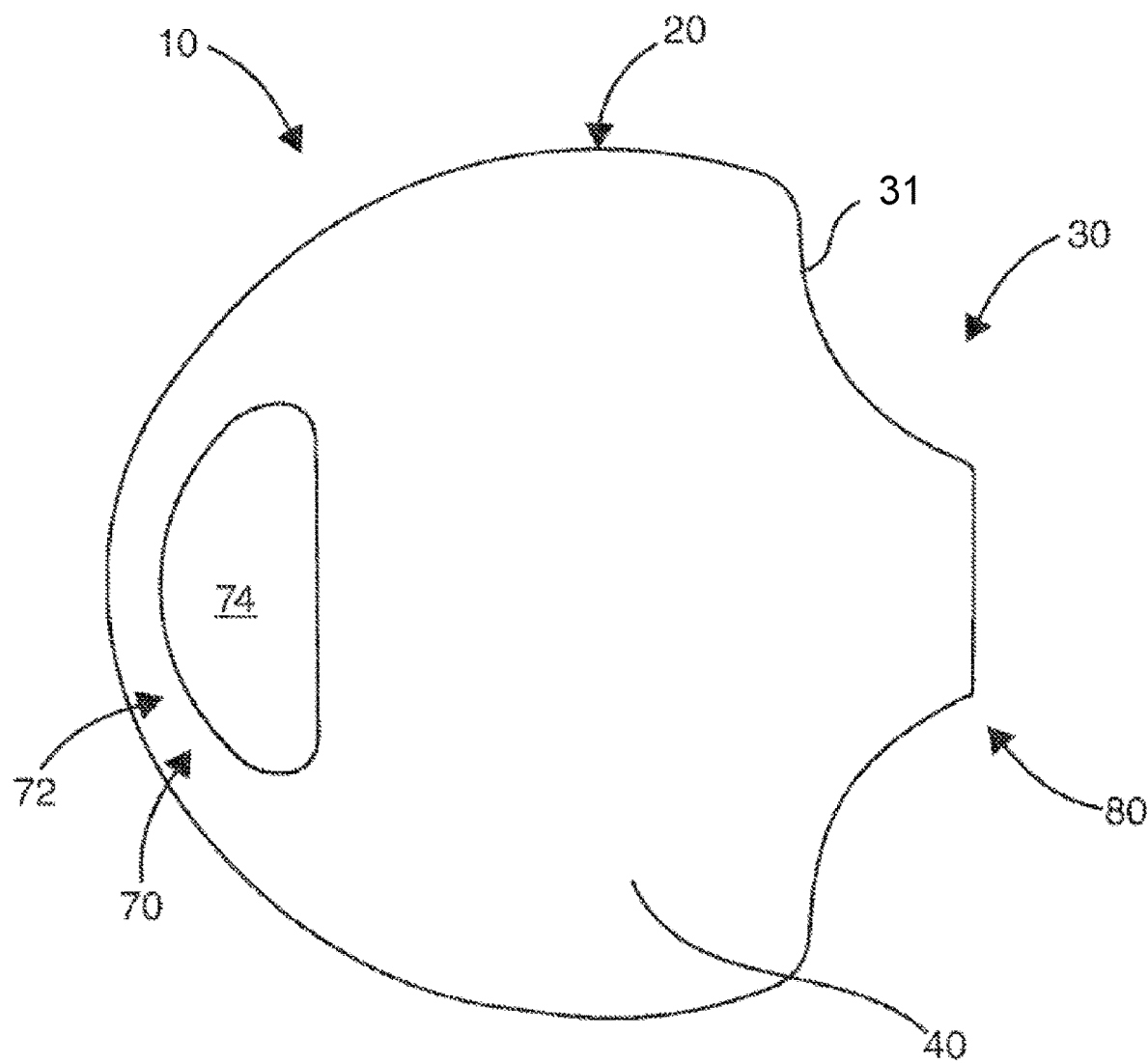
FIG. 1 is a top view of a nasal annual cover, wherein the bottom view is identical to the top view.

The nasal cannula cover of the present invention provides a sanitary location to store and protect the nasal prongs of a nasal cannula when the latter is not in use. The cover is designed so that the nasal cannula can be plugged into the cover such that the nasal prongs extend into a cavity of the cover thereby shielding them from contact with a contaminant such as bacteria, pathogen, virus, dirt or the like. The areas that contact the user such as the prongs and the area immediately around and between the prongs are sealed and protected within the nasal cannula cover. The user never has to touch and contaminate these sensitive areas of the cannula in order to use the nasal cannula cover.

Turning now to the drawings, one embodiment of a nasal cannula cover 10 is illustrated in the numerous figures attached hereto. The cover has a body 20 formed from a durable material, preferably a polymer. Polyurethane is preferred in one embodiment. A one-piece construction is illustrated, but it is to be understood that the cover can be formed from two or more pieces of the same or different materials as desired. While the cover is illustrated in a semi-circular form, it should be apparent that other shapes can be utilized as long as the cover functions in its intended use to protect the nasal prongs of a nasal cannula. The body, as illustrated in the figures, a front end 30 which includes a cavity 32 extending inwardly from an outer surface 31 thereof, a top 40 and a bottom 50 that extend laterally a greater distance than sides 60 which connect the top and bottom. An attachment fixture 70 is shown located at a rear end of the body.

The cavity 32 extends a sufficient depth, measured from an outer surface of the body 20, into an interior portion of the body such that the nasal prongs of the nasal cannula can be stored therein. In some embodiments it is desirable that the nasal prongs fit within the cavity such that the distal ends of the prongs are not in contact with any surface of the cavity. In some embodiments, the body 20 has at least one vent 22 that extends from an outer surface of the body to the cavity for providing air and moisture exchange. Moisture is allowed to escape through the vent and be replaced with fresh air that can circulate around the nasal prongs and an airtight seal would otherwise trap moisture inside the device and promote bacterial growth.

Figure 2:
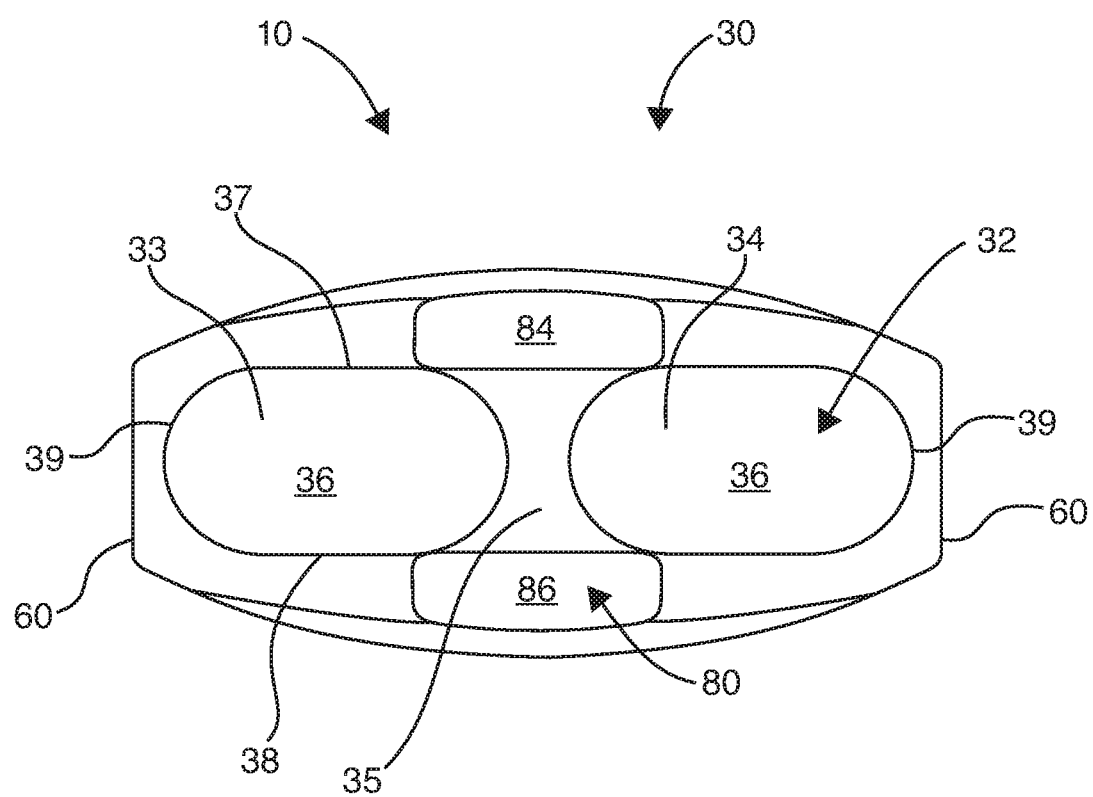
FIG. 2 is a front view thereof.
Figure 3:
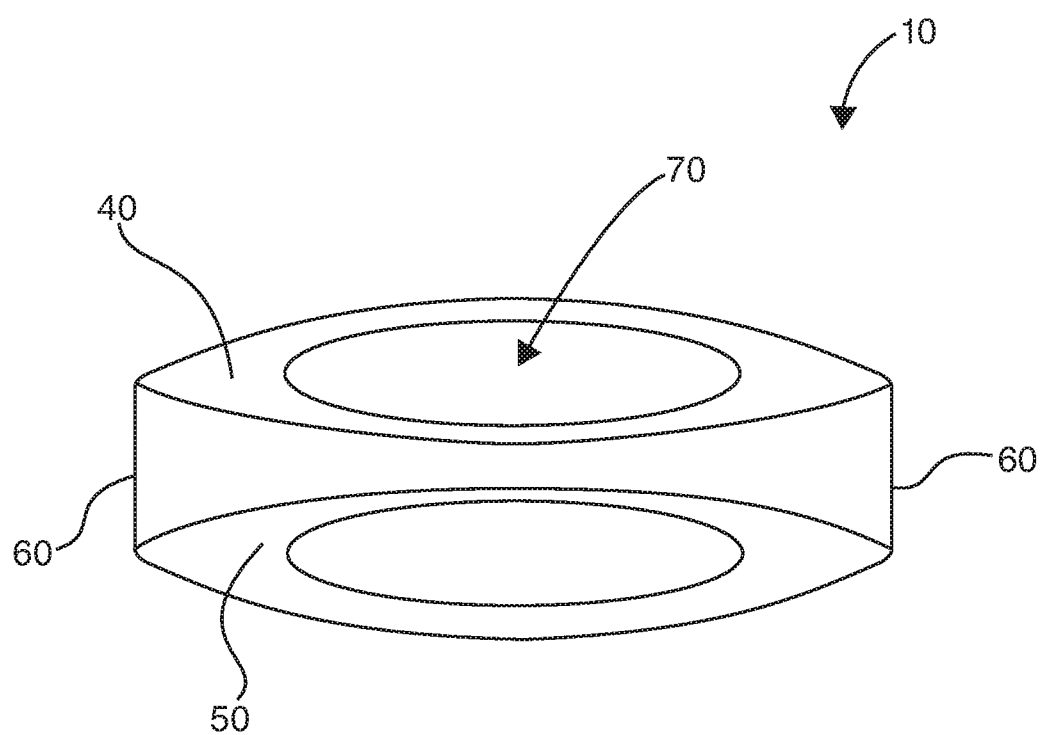
FIG. 3 is a rear view thereof.
Figure 4:
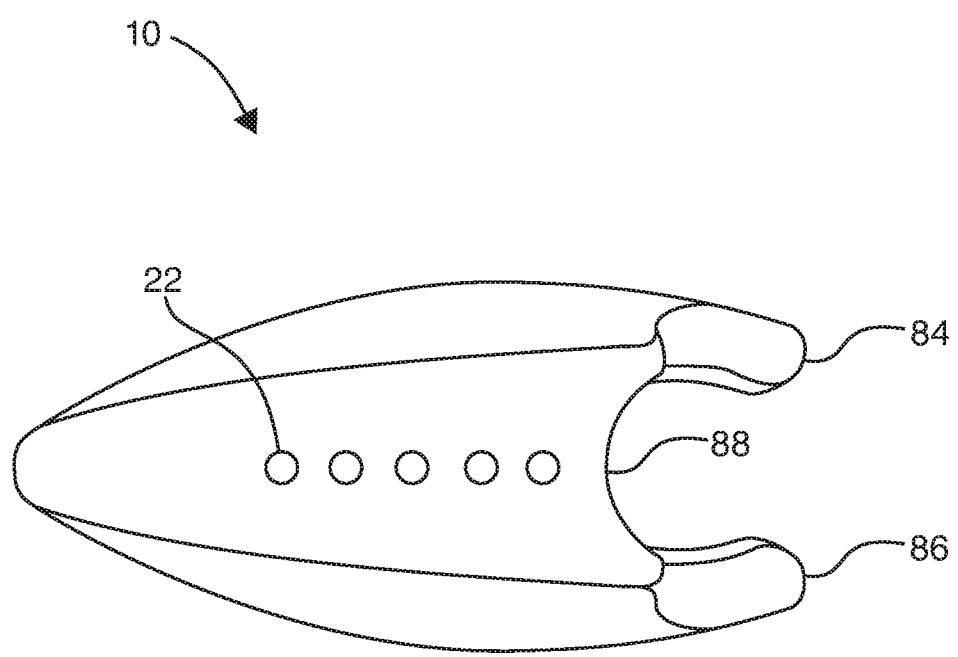
FIG. 4 is a first side view thereof, wherein the other side is identical thereto.
Figure 5:
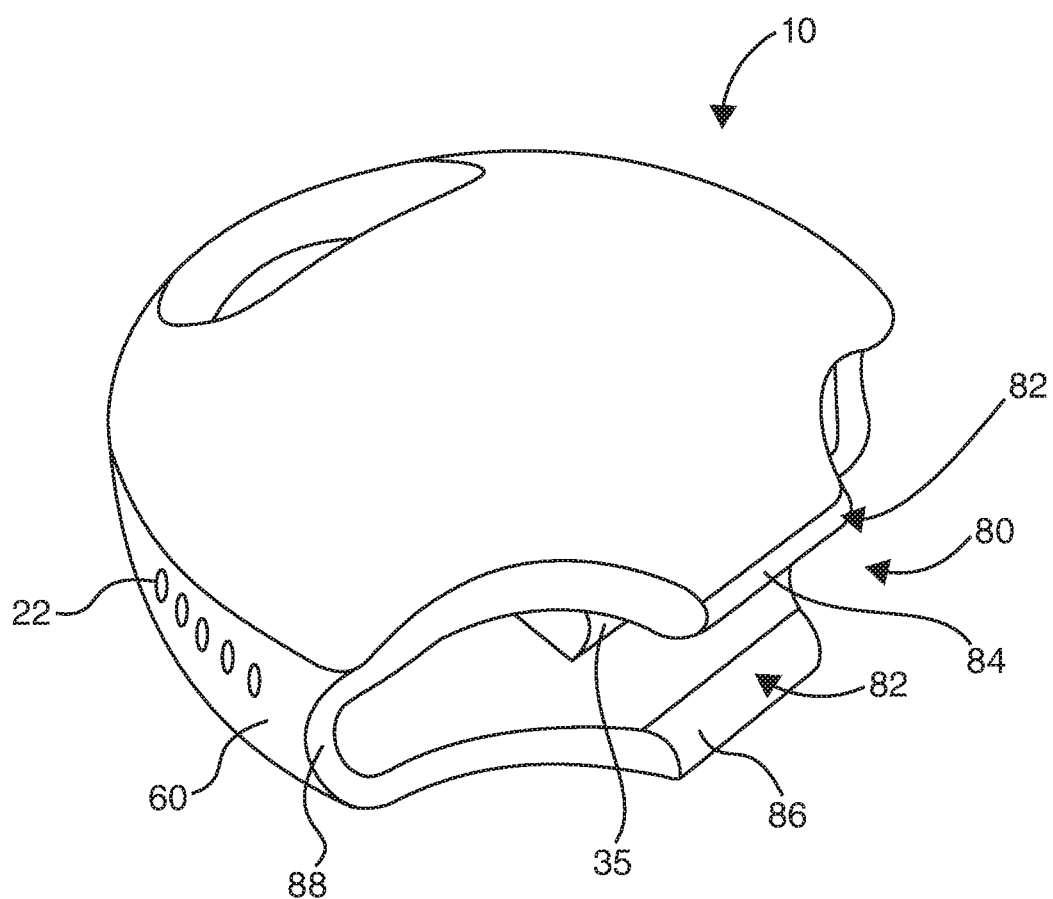
FIG. 5 is a front perspective view thereof.
Figure 6:
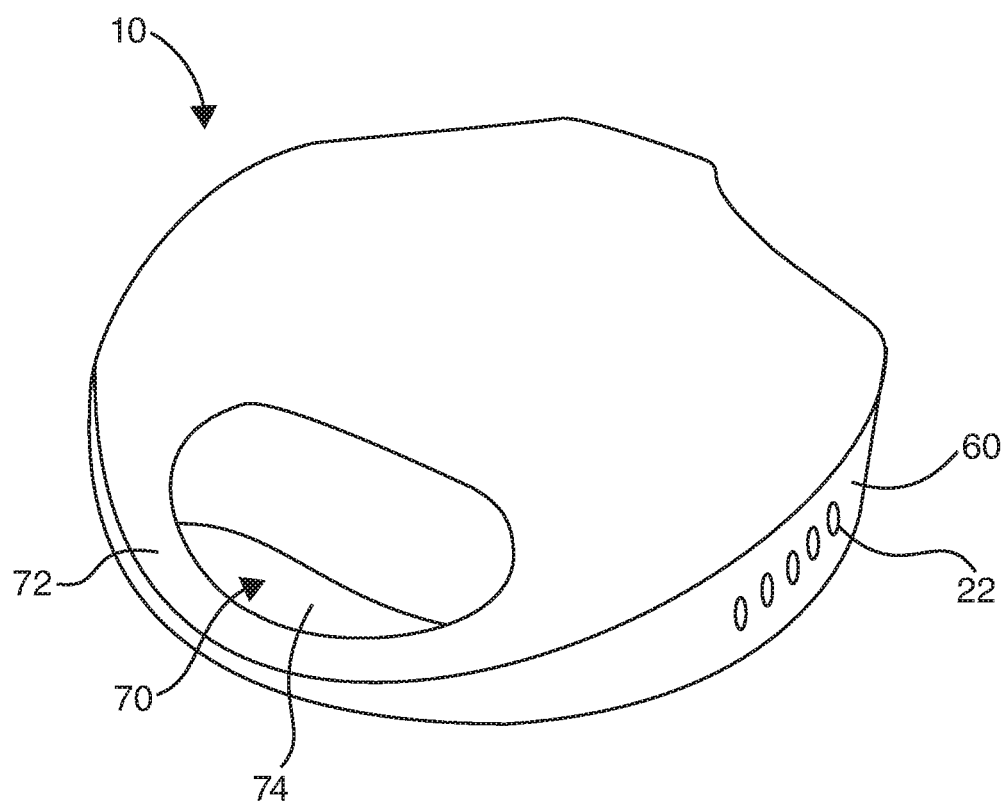
FIG. 6 is rear perspective view thereof.
Figure 7:
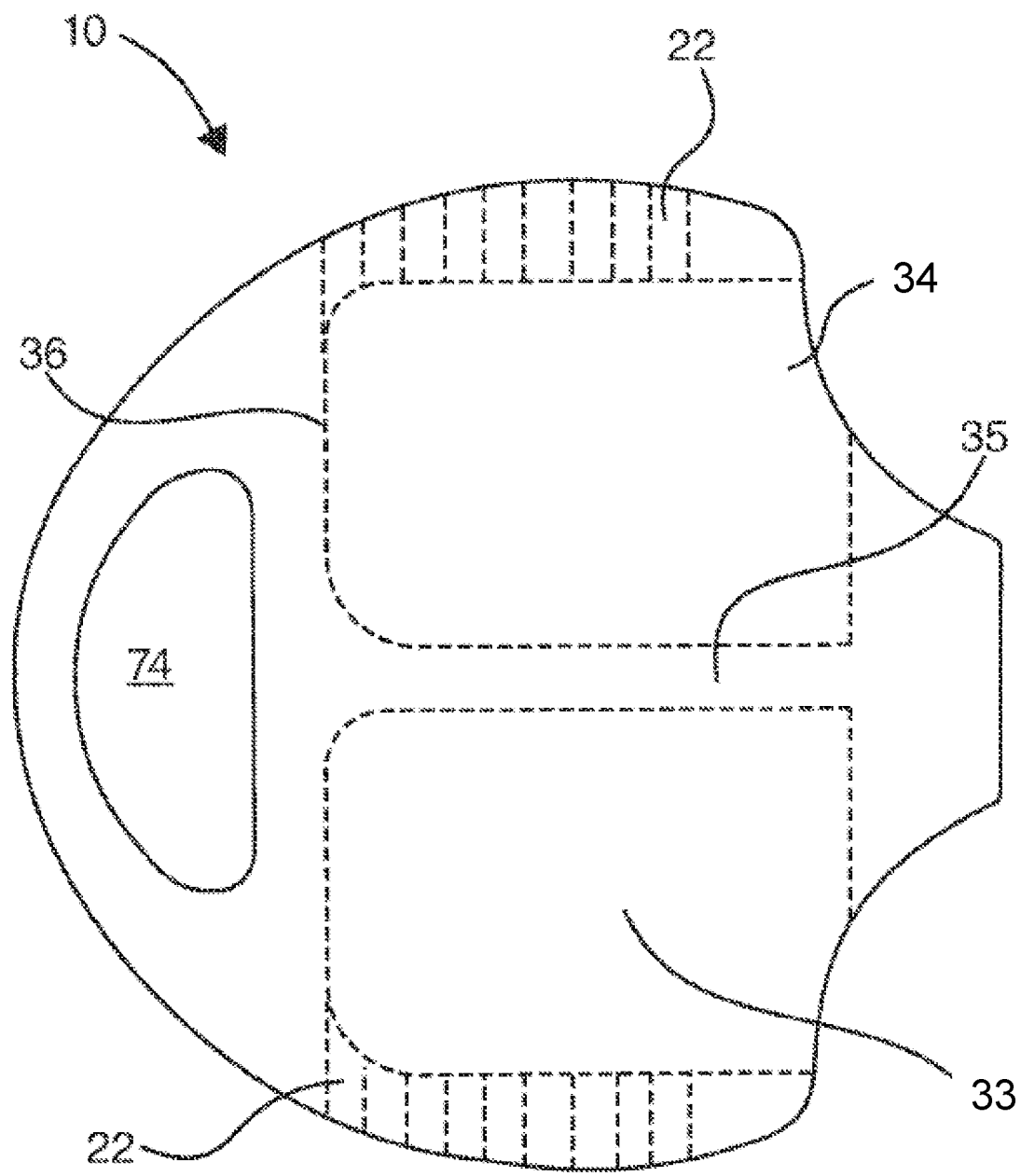
FIG. 7 is a top view illustrating the air vents extending into the cavity as well as the depth of the cavity.

As show in FIGS. 2, 5 and 7, in one embodiment a divider 35 is present in the cavity and separates the cavity into a first section 33 adapted to accept a first prong of the nasal cannula and a second section 34 adapted to accept a second prong of the nasal cannula. The divider prevents cross contamination between nasal prongs of the nasal cannula. In a preferred embodiment, the divider 35 extends from the base 36 of the cavity 32 up towards the front end 30 of the body 20 a distance of at least 50% or at least 75% or 85% of the total height of the cavity, measured from the base 36 of the cavity to the outer surface of the body. In FIG. 2, the divider 35 is shown extending between a first wall 37 of the cavity and a second wall 38 of the cavity. The first wall 37 of the cavity 35 extends laterally within the top of the cover and the second wall 38 extends laterally within the bottom of the cover. The sides 60 of the cover include the side walls 39 of the cavity 32. The cavity is generally enclosed on all sides except for at the front end in order to allow insertion of the nasal cannula.

A nasal cannula connector 80 is provided to temporarily connect the nasal cannula to the cover 10. The nasal cannula cover 10 includes a fastener 82 that is adapted to releasably engage and connect to the nasal cannula for storage of the nasal prongs of the nasal cannula within the cavity. The nasal cannula connector 80 releasably secures the nasal cannula utilizing pressure via the fastener 82 which preferably has a clamping structure.

Figure 8:
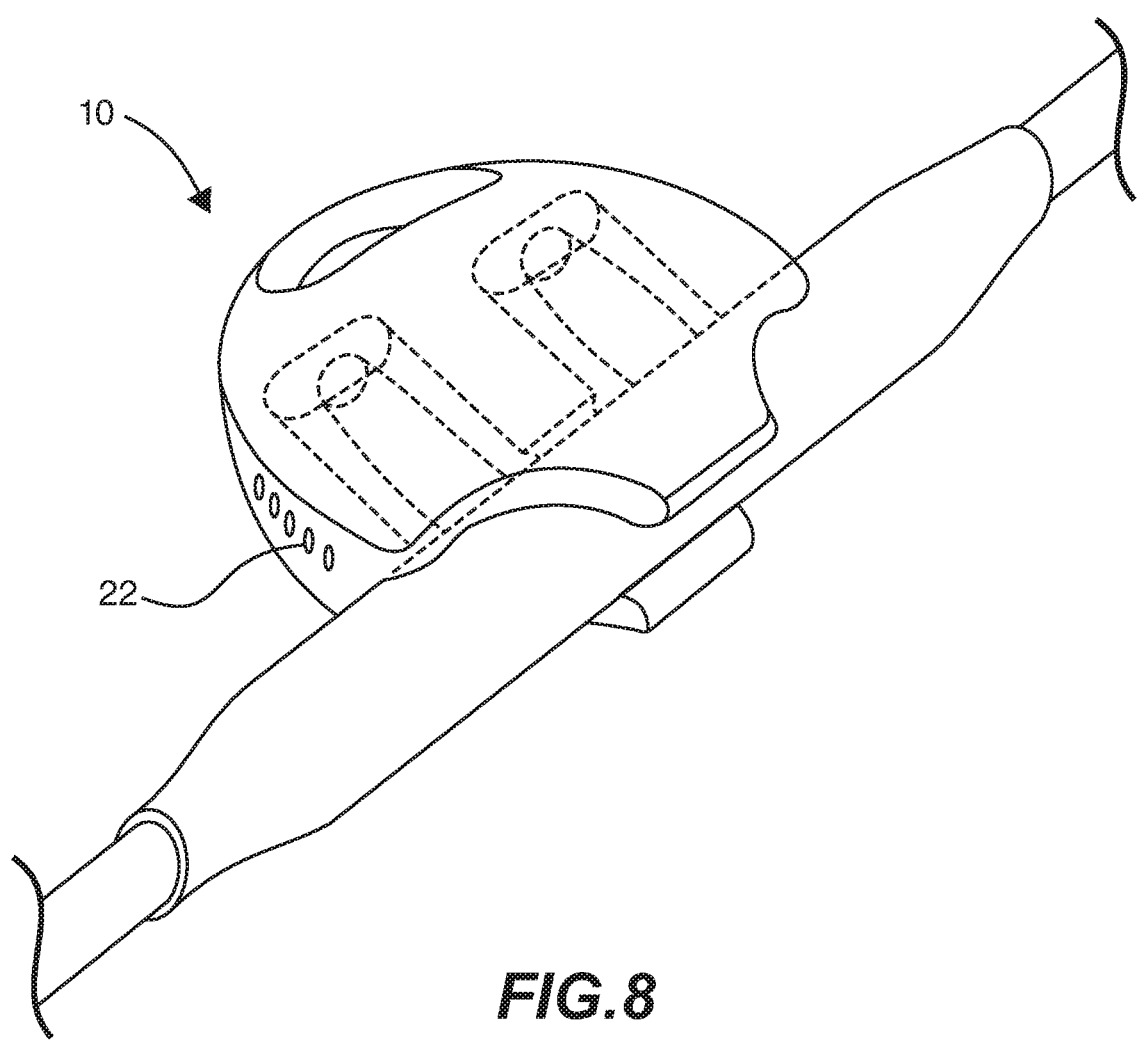
FIG. 8 is a front perspective view of the nasal cannula cover in use having a nasal cannula secured therein.

In one embodiment the fastener 82 includes a first arm 84 located adjacent the first wall 37 of the cavity 32 and a second arm 86 located adjacent the second wall 38 of the cavity 32, wherein the first arm 84 and the second arm 86 are adapted to releasably connect the nasal cannula therebetween, for example as illustrated in FIG. 8. The arms 84,86 preferably curve inwardly, outwardly from the cover and around the outer surface of nasal cannula 10 when the nasal prongs of the nasal cannula are inserted into the cavity 32. As illustrated in the side view of FIG. 2, in one embodiment one or more arms 84,86 of the nasal cannula connector are curved in shape. As can be imagined, in some embodiments only a single arm is needed in order to releasably connect the nasal cannula between the arm and a nasal cannula seat 88 of the body.

Nasal cannula seat 88 is present at the top of the cavity 32 at ends of the first wall 37 and second wall 38 which include respectively, a first seat 88 and a second seat 88 adapted to contact a portion of the nasal cannula when releasably connected to the cover 10 for storage. The first seat 88 and second seat 88 are preferably formed as curved sections which correspond to a curved portion of the nasal cannula and thereby form a seal with the nasal cannula when connected to the cover.

In order to facilitate connection of the nasal cannula cover 10 to another object, for example a bag or carrying case for a portable oxygen concentrator or source of oxygen or a hook or other structure, the cover includes an attachment fixture 70 which includes a handle 72 formed on or connected to the body 20 that allows connection to the object for hanging otherwise connecting the cover to the object.

In a preferred embodiment as illustrated, the handle 72 includes an aperture 74 extending completely through the body, such as through the top and bottom surfaces. The aperture 74 of the handle 72 is not connected to, and is separate and thus isolated from the cavity. The presence of the aperture allows use of the cover with a line, cord, hook, clip or the like to allow attachment directly or indirectly to another object.

For the avoidance of doubt, it is to be understood that the nasal cannula cover of the present invention can include one or more of each of the embodiments described herein. In some cases, it is desirable to provide a nasal cannula cover with each of the embodiments presented herein and some other nesting deterrent comprise less than all of the embodiments described.

In accordance with the patent statutes, the best mode and preferred embodiment have been set forth; the scope of the invention is not limited thereto, but rather by the scope of the attached claims.

What is claimed is:

1. A cover for use with a nasal cannula, comprising:
   a body having a cavity positioned therein, wherein the body includes a first wall located on a first side of the cavity and a second wall located on a second, opposite side of the cavity in a thickness direction thereof, wherein the first and second walls are outermost walls of the body;
   a divider that separates the cavity into a first section having a closed distal end and that is configured to accept a first prong of the nasal cannula therein, and a second section having a closed distal end and that is configured to accept a second prong of the nasal cannula therein, wherein the divider permanently extends between and from the first wall and the second wall; and
   a connector that is configured to compressively grip the nasal cannula and retain the first and second prongs of the nasal cannula within the cavity.

2. The cover of claim 1 wherein the body has at least one air vent located at a distal end thereof opposite the connector, that extends from an outer surface of the body to the cavity for providing air exchange.

3. The cover of claim 2 wherein the divider extends from a base of the cavity at least 50% of the total height of the cavity, where the total height of the cavity is measured from a base of the cavity to the outer surface of the body.

4. The cover of claim 1 wherein the connector includes a first arm located adjacent the first wall of the cavity and a second arm located adjacent the second wall of the cavity, wherein the first arm and the second arm are configured to releasably grip the nasal cannula therebetween.

5. The cover of claim 1 wherein the cover further includes a handle formed on or connected to the body that facilitates connection of the cover to an object, wherein the handle includes or defines an aperture extending completely through the body, and wherein the aperture is not connected to the cavity.

6. A cover for use with a nasal cannula having a main line and a pair of nasal cannula prongs extending therefrom in an axial direction, the cover comprising:
   a body having a cavity that is configured to receive therein the pair of nasal cannula prongs, wherein the body is generally closed at a distal end thereof; and
   a connector that is configured to directly contact a portion of the nasal cannula and releasably connect the nasal cannula to the cover, wherein the connector is located at an outer edge of the cover at a proximal open end thereof located opposite the distal end such that the nasal cannula is insertable into the connector and receivable in the cavity in a direction parallel to the axial direction, wherein a first section of the cavity is configured to receive one of the pair of nasal cannula prongs therein and wherein a second section of the cavity is configured to receive the other one of the pair of nasal cannula prongs therein while the main line is coupled to the connector, and wherein the body is positioned between, and extends continuously in a lateral direction between, the first and second sections of the cavity, wherein the lateral direction is oriented in a direction perpendicular to a direction of receipt of the cannula prongs in the cavity, wherein the body has first and second opposed ends adjacent to the outer edge of the cover spaced apart in the lateral direction, and wherein a portion of the connector that is configured to directly contact the nasal cannula is spaced away, in the lateral direction, from the first and second ends.

7. The cover of claim 6 wherein the body has at least one air vent, located at the distal end thereof, that extends from an outer surface of the body to the cavity for providing air exchange.

8. The cover of claim 6, further including a divider positioned in the cavity that separates the cavity into the first section and the second section.

9. The cover of claim 6 wherein the body has a first wall and a second wall defining the cavity therebetween, and wherein the cover includes a first seat and a second seat spaced away from the connector and configured to directly contact and compress a portion of the nasal cannula when the nasal cannula is releasably connected to the cover, and wherein the first and second seats are offset from the connector in the lateral direction.

10. The cover of claim 6 wherein the connector includes a first arm and a second opposed arm defining a gap therebetween which is sized to receive the main line of the nasal cannula, located at a base of the prongs, therebetween and compressively grip the main line therebetween, and wherein the connector is configured to directly contact the portion of the nasal cannula at a location spaced away, in the lateral direction, from the first and second ends.

11. The cover of claim 6 wherein the body includes a first wall located on a first side of the cavity and a second wall located on a second, opposite side of the cavity, wherein the first and second walls are oriented generally parallel to each other and are configured to be oriented generally parallel to the main line when the cannula is coupled to the connector.

12. The cover of claim 6 wherein the lateral direction intersects the first and second sections of the cavity.

13. The cover of claim 6 wherein the connector is configured to receive the cannula therein such that at least a portion of the nasal cannula in direct contact with the connector and aligned with a base of each prong, relative to the axial direction of each prong, is positioned externally of the cavity.

14. The cover of claim 6 wherein the lateral direction is parallel to the main line at locations where the main line is directly coupled to the connector, and wherein at least part of the connector is positioned in a center of the cover along the lateral direction.

15. The cover of claim 6 wherein the connector includes a first arm and a second opposed arm defining a gap therebetween which is sized to receive the main line of the nasal cannula therein, wherein the arms are configured to compressively grip the main line therebetween, wherein each arm curves about the main line when the main line is received in the gap, and wherein each arm curves to define a widest location of the gap then extends to define a narrower portion of the gap at a distal end of the arms.

16. A nasal cannula assembly comprising:
a nasal cannula including a main line and a pair of nasal cannula prongs extending therefrom in an axial direction; and
a cover comprising:
a body having a cavity positioned therein, wherein the cavity is sized to simultaneously receive both of the nasal cannula prongs therein such that an outer surface of each prong, extending between a distal end of each prong and the main line of the cannula, is not in contact with any surface of the cavity; and
a connector that is configured to releasably connect the nasal cannula to the cover, wherein the connector includes a first arm located on a first side of the body adjacent the cavity and a second arm located on a second side of the body adjacent the cavity, wherein the first arm and the second arm are configured to releasably compressively grip the nasal cannula therebetween, wherein the connector is located at an outer edge of the cover at a proximal open end thereof such that the nasal cannula is insertable into the connector and receivable in the cavity in a direction parallel to the axial direction, wherein the nasal cannula is connectable to the cover by the connector such that at least a portion of the nasal cannula in direct contact with the cover and aligned along the main line with a base of each prong, along the axial direction of each prong, is positioned externally of the cavity.

17. The assembly of claim 16 wherein the cover is closed at a distal end thereof located opposite the proximal open end.

18. The assembly of claim 16 wherein a first section of the cavity is configured to receive one of the pair of nasal cannula prongs therein and wherein a second section of the cavity is configured to receive the other one of the pair of nasal cannula prongs therein while the main line is coupled to the connector, and wherein the body is positioned between, and extends continuously in a lateral direction between, the first and second section of the cavity, wherein the lateral direction is oriented in a direction perpendicular to the direction of insertion of the cannula in the cavity.

19. The assembly of claim 16 wherein the at least a portion of the nasal cannula is in direct contact with the connector and is directly positioned between the base of the prongs of the cannula in a direction extending parallel to the at least a portion of the nasal cannula.

20. The assembly of claim 16 wherein the base of each prong is positioned, in the lateral direction, between a seat of the cover that is in direct contact with the nasal cannula, and at least part of the connector that is in direct contact with the nasal cannula.

21. A method for covering a nasal cannula comprising:
accessing a nasal cannula including a main line and a pair of nasal cannula prongs extending therefrom in an axial direction;
accessing a cover including a connector and a body having a cavity positioned therein, wherein the connector includes a first arm located on a first side of the body adjacent the cavity and a second arm located on a second side of the body adjacent the cavity; and
coupling the nasal cannula to the connector of the cover such that both of the cannula prongs are received in the cavity, and such that the first arm and second arm releasably grip the nasal cannula therebetween, wherein the connector is located at an outer edge of the cover at a proximal open end thereof located opposite a generally closed distal end such that the nasal cannula is inserted into the connector and received in the cavity in a direction parallel to the axial direction, wherein the cavity receives both of the nasal cannula prongs therein such that an outer surface of each prong, extending between a distal end of each prong and the main line of the cannula, is not in contact with any surface of the cavity, and wherein the connector directly contacts and receives the cannula therein such that at least a portion of the connector in contact with and gripping the nasal cannula is positioned between the prongs in a lateral direction extending along a length of the main line.

22. The method of claim 21 wherein the body includes a first wall located on a first side of the cavity and a second wall located on a second, opposite side of the cavity, wherein the first and second walls are oriented generally parallel to each other and generally parallel to the main line, located at a base of the prongs, when the cannula is received therein, wherein the first arm is formed as a continuous component with the first wall and is an outermost surface of the connector, and wherein the second arm is formed as a continuous component with the first wall and is an outermost surface of the connector, and wherein the pair of nasal cannula prongs are inserted into the cavity while at least part of the main line aligned with the cover remains positioned outside the cavity.

* * * * *